United States Patent [19]

Erickson

[11] Patent Number: 4,515,920

[45] Date of Patent: May 7, 1985

[54] SYNTHESIS OF PEPTIDES AND PROTEINS

[75] Inventor: Bruce W. Erickson, Closter, N.J.

[73] Assignee: The Rockefeller University, New York, N.Y.

[21] Appl. No.: 605,308

[22] Filed: Apr. 30, 1984

[51] Int. Cl.$^3$ .................... C08F 210/00; C07C 103/52
[52] U.S. Cl. .............................. 525/54.11; 525/54.1; 260/112.5 R
[58] Field of Search ........................... 525/54.11, 54.1; 260/112.5 R

[56] References Cited

U.S. PATENT DOCUMENTS 3,956,219  5/1976  Smithwick, Jr. ............ 260/112.5 R
4,038,469  7/1977  Walker et al. ................... 525/54.11
4,062,746 12/1977  Rich et al. .................... 260/112.5 R

*Primary Examiner*—Delbert R. Philips
*Attorney, Agent, or Firm*—Wyatt, Gerber, Shoup, Scobey and Badie

[57] ABSTRACT

Solid phase synthesis of peptides and proteins have been improved by the use of a trifunctional segment, one functional group of which is bound to a solid support, the other two functional groups being available as substrates upon which identical proteins are synthesized.

4 Claims, 7 Drawing Figures

FIG. 1

FIG. 2

(PEPTIDE-ARM)$_2$ - CORE - HEAD - RESIN

```
LEVEL  A       B        C        D        E        F        G        H
STRAND
        1       2        3        4        5        6        7        8
1    NH₂-Ser+++Thr+++VAL+++Thr+++ALA+++Arg+++GLN+++Pro
            |        |                |        |            | |    +
            |        |                |        |            | |    +
            |        |                |        |            | |    +
        16      15      14       13       12       11       10       9
2    Pro+++Ser+++ILE+++Ser+++TYR+++Thr+++VAL+++Asn
     +
     +
     +  17      18       19      20       21       22       23      24
3    Asn+++Thr+++ALA+++Thr+++VAL+++Arg+++LEU+++Pro
            |        |                |        |            | |    +
                                                              |    +
        31      30       29       28       27       26      +25
4    NH-CO-Gly+++ILE+++Ser+++LEU+++Thr+++TYR+++Asn
     +
     HOOC-Dab
     +
        31      30       29       28       27       26       25
4    NH-CO-Gly+++ILE+++Ser+++LEU+++Thr+++TYR+++Asn
            |        |                |        |            | |    +
                                                              |    +
        17      18       19       20       21       22       23    +24
3    Asn+++Thr+++ALA+++Thr+++VAL+++Arg+++LEU+++Pro
     +
     +
     +
        16      15       14       13       12       11       10       9
2    Pro+++Ser+++ILE+++Ser+++TYR+++Thr+++VAL+++Asn
            |        |                |        |            | |    +
                                                              | |  +
        1       2        3        4        5        6       7   +8
1    NH₂-Ser+++Thr+++VAL+++Thr+++ALA+++Arg+++GLN+++Pro
     LEVEL A       B        C        D        E        F        G        H
```

FIG. 7

SYNTHESIS OF PEPTIDES AND PROTEINS

BACKGROUND OF THE INVENTION

This invention relates to improvements in the solid phase synthesis of peptides and proteins.

The classical synthesis of peptides has used the solution method in which a protected amino acid or peptide fragment has been reacted in solution with another protected amino acid or protected peptide chain. At each step of the synthesis the desired product has been separated from the reaction medium and at least partially purified before continuing to the next step. The procedure is time-consuming and tedious. However, it is capable of producing high-purity products. These procedures have been used to produce oxytocin, insulin, adrenocortocotropin and other proteins.

In 1962, Merrifield introduced the solid phase method of peptide synthesis. In this procedure, the amino acid corresponding to the carboxyl end of a peptide chain was attached to an insoluble support, normally a resin through the alpha carboxyl group and the chain was extended toward the amino end by stepwise coupling of activated amino acid derivatives. Filtration and thorough washing of the solid phase removed soluble by-products and excess reagents but retained the extended peptide chain without loss. After completion of the chain the peptide was removed from the support and purified.

The initial procedure has been modified by attaching an activated amino acid by its alpha amino group to the resin support and extending the chain towards the carboxyl end. Procedures have also been devised in which a functional group of an amino acid other than the alpha amino group or the carboxyl group has served as the link to the solid support. However, the vast majority of peptides and proteins that have been synthesized using solid phase technology have followed the original procedure in which the peptide has been extended toward the amino end. Generally the procedure is conducted by the following steps:

1. Attachment of an amino acid with a protected amino group to a resin support through its carboxyl group.
2. Removal of the protecting group from the amino group.
3. Couple the supported amino acid with a second amino acid in which the amino group is protected, by reaction between the deprotected amino group of the supported amino acid and the carboxyl group of the second amino acid.
4. Removal of the protecting group from the amino group of the second amino acid.

Steps 2-4 above are repeated as many times as is necessary to produce the desired product.

At each stage of the synthesis, the support carrying the synthesized product is recovered by filtration and thoroughly washed to remove insoluble impurities.

As those skilled in the art will be aware, there are many variations of the basic theme. For example, eleven of the twenty common amino acids bear functional groups that are usually protected during the synthesis with protecting groups which will not interfere with the overall synthesis and can be readily removed when it is desirable to do so. For example, the guanidino group of arginine has been protected by the nitro group or the 4-toluensulfonyl group. The epsilon amino group of lysine has been protected by the benzyloxylcarbonyl group. The beta carboxyl group of aspartic acid, the gamma carboxyl group of glutamic acid, the beta hydroxyl groups of serine and threonine, and the phenolic hydroxyl group of tyrosine have been protected by the benzyl group. Other protecting groups are known and have been employed to protect the extra functional groups of the named amino acids as well as other polyfunctional amino acids.

Another important variation is to increase the length of the growing chain by coupling the supported amino acid or peptide with a separately synthesized peptide fragment. Still another is to remove the peptide from the support at an intermediate stage in the synthesis, purify it and then reattach it to the support before continuing the synthesis. They have been extensively utilized to produce large numbers of peptides and proteins. Heretofore, the procedures have been as described above. The desired product has been constructed by growth originated from a single link to the selected support.

After the peptide has been assembled on a solid support, it must be removed from the support by a suitable cleavage reaction. The choice of the cleavage reagent depends primarily on the bond linking the peptide to the support. But the constituent amino acids of the peptide, the nature of their side chain protecting groups, and the structure of the final derivative desired must also be considered. Peptide removal has been effected by acidolytic or alkaline hydrolysis, aminolysis, alcoholysis and other cleavage methods. Acidolysis is by far the most widely employed procedure.

A large number of acidolytic reagents are known. These include, for example, bromine-free hydrogen bromide in trifluoroacetic acid (TFA) or in acetic acid. The method of choice for most investigators is liquid hydrogen fluoride and anisole at 0° C. for about one hour. A particular advantage of this reagent is that it removes all side chain protecting groups and cleaves the most widely employed anchoring bond in one step.

The most widely employed anchoring bond for the procedure in which the chain is extended toward the amino end is the ester group in which the carboxyl group of the first amino acid in the chain is attached through a benzyl group on a polystyrene support resin. The benzyl group is generated by chloromethylation of polystyrene with chloromethyl methyl ether and a Lewis acid catalyst. The first amino acid to be attached to the support is reacted as an amino-protected salt, typically the cesium salt.

A wide variety of solid supports have been studied and utilized in the solid phase synthetic methods. These include polystyrene cross-linked with divinylbenzene, phenol-formaldehyde resins, cellulose, and silicon. The support which has achieved widest acceptance is polystyrene cross-linked with about 1% to 2% divinylbenzene.

The alpha amine protecting group which has proved to be most useful in solid phase synthesis is the tertiary butyloxycarbonyl group (Boc). This group is readily substituted on the amino group and removed when necessary with minimum disruption of the peptide. However, practically all the protecting groups used in conventional peptide syntheses have been successfully employed in solid phase synthesis. These include, for example, benzyloxycarbonyl, triphenylmethyl, tertiary amyloxycarbonyl, furfuroxyloxycarbonyl and 2-nitrophenylsulfonyl.

This brief overview of the solid phase synthetic method has been provided to indicate that the procedure is well known and has been intensively studied. Principal emphasis has been on procedures in which the peptide grows towards the amino end. Procedures for extending the peptide toward the carboxyl end have also been extensively studied, but because of inherent disadvantages, such as racemization, have not been as widely employed. Those skilled in the art, however, will immediately recognize from a study of this specification that the improvements described herein are applicable to all types of solid phase peptide syntheses.

The solid phase procedures have proven to be a revolutionary advance in peptide synthesis.

THE INVENTION

A new method has now been discovered which markedly improves the efficiency of the conventional procedure. In this novel approach to solid phase peptide synthesis two or more peptides or proteins are produced from a trifunctional linking molecule. In the linking molecule one of the functional groups is bound to the resin, either directly or through a spacer group. The other two functional groups serve as anchors for the peptide chains. Alternatively, the other two functional groups can each be joined to a second trifunctional molecule, two functional groups of which can serve as anchors for peptide chains. This type of geometric growth from the single point of attachment to the resin can be repeated any selected number of times such as 4 to 6 times to increase the number of anchors available for peptide chains.

The construction of the peptide or protein chains is in accordance with standard solid phase techniques as outlined above. The advantage is that the amount of useful product produced can be greatly increased per unit time. Theoretically, it can be doubled, quadrupled, etc. In practice, however, the synthetic procedures of this invention, as with most synthetic procedures, do not proceed with one hundred percent efficiency.

An important feature of the invention is the selection of the trifunctional molecule. It will contain one functional group through which it will be anchored to the resin, and two functional groups from which the peptides or proteins may be grown. Typically, it will contain a carboxyl group and two amino groups joined to an aliphatic or aromatic moiety. The functional groups normally will be positioned symmetrically, but such placement is not essential. As will be apparent from the above general discussion of solid phase synthesis, it is preferred that the linking molecule be one in which there is a single carboxyl group and two amino groups. However, in special circumstances, it may be desirable to have one amino group and two carboxyl groups. As this description proceeds, it will become apparent that functional groups other than carboxyl and amino groups can be employed.

In all applications of this invention it will be necessary to remove the final product from the resin support. In some procedures it will be desirable to remove the linking segment from the peptide or protein chains. In others it will not be necessary to do so.

It will be apparent, therefore, that there is a wide range of choices in selecting the linking molecule. One of the simplest linking molecules would be 3,5-diaminobenzoic acid. This molecule could be linked directly to a polystyrene support through a benzyl group generated by chloromethylation of crosslinked polystyrene as described above. This linking molecule, however, is not the molecule of choice for a number of reasons. One is that an aromatic amino group is not as reactive as an aliphatic amino group. Another is that the single carboxyl group does not move the linking molecule far enough away from the support to allow maximum flexibility of reactants. It will be remembered that the volume of a sphere increases as the cube of the radius. Therefore, the further a particular reaction center is from the resin support, the more space there is for the reactants, and the less problem with steric hindrance. It is preferable, therefore, to include a spacer molecule between the carboxyl group and the resin and to replace the amino group with an aminomethyl group. Thus a compound such as 3,5-bis(aminomethyl)benzoic acid is preferable to its next lower homolog. Any of a number of spacer molecules can be used with this compound, for example glycine. The glycine can be linked to a polystyrene resin through its alpha-carboxyl group in the conventional manner and to the linking molecule through its alpha-amino group by forming a peptide bond. Each of the amino methyl groups can serve as anchors for a growing peptide or protein chain.

The foregoing discussion can be illustrated by the following structure where R is the resin support.

It will be apparent from the foregoing discussion and structural formula that each linking molecule gives rise to two peptides. It will also be apparent that if each peptide is replaced with a 3,5-bis(aminomethyl)benzoic acid moiety, the resulting structure will have the potential of anchoring four peptide chains.

When peptides grown on the structure shown above are treated with liquid hydrogen fluoride in anisole at 0° C. for one hour, the complete molecule including the linking molecule and the spacer will cleave from the resin. If it is desirable to separate the peptides from the linking molecule the two must be joined by a linkage other than a peptide bond.

The foregoing rather specific discussion should assist in understanding the invention. There follows a more generalized discussion which will illustrate more fully the scope of the invention. The discussion will be assisted by reference to FIGS. 1, 2 and 3.

Figure 1:
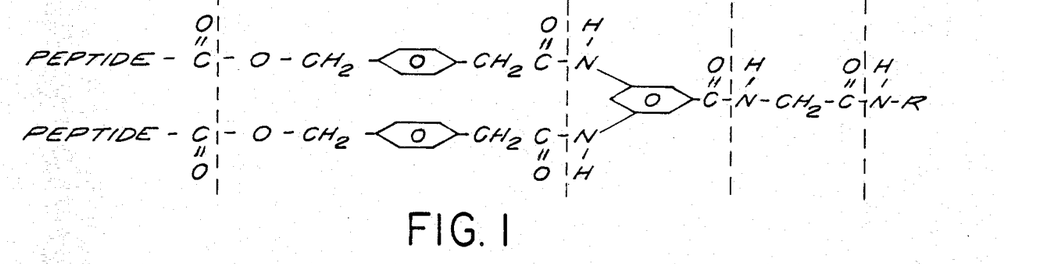
Figure 2:
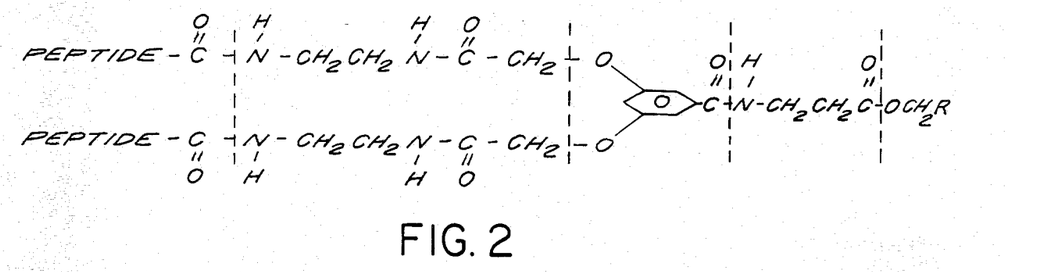

FIG. 1 shows a type of linking segment joined to two peptides by a benzyl ester group. In FIG. 2 the peptides are joined to the linking molecule by an amide group. If the product of FIG. 1 is treated with liquid hydrogen fluoride in anisole at 0° C., the peptides will cleave from the linking molecule. If the product of FIG. 2 is similarly treated cleavage will occur at the ester link to the resin. The resulting hydrolyzed product will contain two peptides joined by the linking segment.

Figure 3:
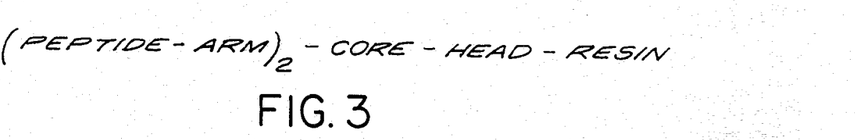

FIG. 3. generalizes the structures of FIGS. 1 and 2.

The linking segment or module of FIG. 1 consists of, reading from left to right, a first unit consisting of identical peptides and identical arms. The second unit is a core moiety, in this instance shown as being symmetrically substituted. The third unit, here called the head, is a spacer segment. It is linked to the fourth unit which may be a solid support resin, through an amide linkage.

The linking module of FIG. 2 is similar to FIG. 1 except for the identity of the segments comprising the structural units.

It will be noted that in FIG. 2 all of the units except the head and the resin are joined together by amide bonds. In FIG. 1 all of the units except the peptide and the arm are joined by amide units. In both figures the joining group which is different from all of the other joining groups is a benzyl ester group which is not stable in the presence of liquid hydrogen fluoride. Amide groups are stable in the presence of the reagent. Therefore, treatment of the products represented by FIG. 1 results in cleavage of the peptides from the linking modules. With the products represented by FIG. 2, however, cleavage occurs at the resin end of the structure.

Those skilled in the art will immediately recognize that the linking segment or module can be readily constructed by known reactions from known products. They will also recognize that the various products comprising the respective units can be replaced with equivalent products.

The products from which the molecule of FIG. 1 may be synthesized are, reading from right to left:
1. An amino substituted support resin.
2. Glycine
3. 3,5-Diaminobenzoic acid
4. Glycine
5. 4-(Hydroxymethyl)phenylacetic acid
6. Peptide.

The products from which the molecule of FIG. 2 may be synthesized are, reading from right to left:
1. A solid support bearing benzyl alcohol groups.
2. Beta-alanine
3. 3-5-Dihydroxybenzoic acid
4. [(2-Aminoethyl)amino]carbonylmethyl bromide.
5. Peptide Quite clearly each of the products can be replaced with an equivalent product and the same results will be obtained, i.e. a linking segment with three functional units, one for combining with the resin support, the other two as starting points for the synthesis of peptides and proteins. The invention therefore comprises a synthetic process for the simultaneous production of two, or a multiple of two, identical peptides or proteins by reacting a trifunctional linking molecule to a resin support through one of the functional groups, synthesizing identical peptide chains by simultaneously reacting identical amino acid or peptide or protein residues with the remaining functional groups, successively reacting the resulting product with additional identical amino acid or peptide residues until the desired peptides are obtained and thereafter separating the peptides from the resin support. As shown above, the peptides can be removed as separate units or as part of a larger molecule containing the trifunctional linking module.

More specifically, the invention could be defined as an improvement in the known solid phase method for the synthesis of proteins or amino acids in which an amino acids or peptide residue is first joined to a solid support such as a resin and the desired peptide or protein formed by the stepwise addition of amino acid or peptide residues. The improvement comprises initially binding a trifunctional module to the solid support through one of the functional groups and thereafter synthesizing identical peptides or proteins by the stepwise addition of amino acid or peptide residues to each of the remaining pair of functional groups.

As explained above the process can be modified by geometrically increasing the number of functional groups available as substrates for the stepwise addition of amino acid or protein residues to the original trifunctional module. By this procedure the number of available substrate functional groups can be increased to as high as 64.

The term "module" as used herein refers to a linking molecule or segment which has three functional groups. It may be separated into several units. The core of the module is the basic unit to which head and/or arm units may be added. The head unit is a spacer group. The module need not include a spacer group, but normally such a group will be present to improve the flexibility of the method for reasons explained above.

The term "residue" as applied to amino acids or peptides refers to that portion of the original molecule which remains at the end of a reaction. For example, the residue of glycine is the glycyl group. The residue of Boc-leucylglycine is the Boc-leucylglycyl group.

Figure 4:
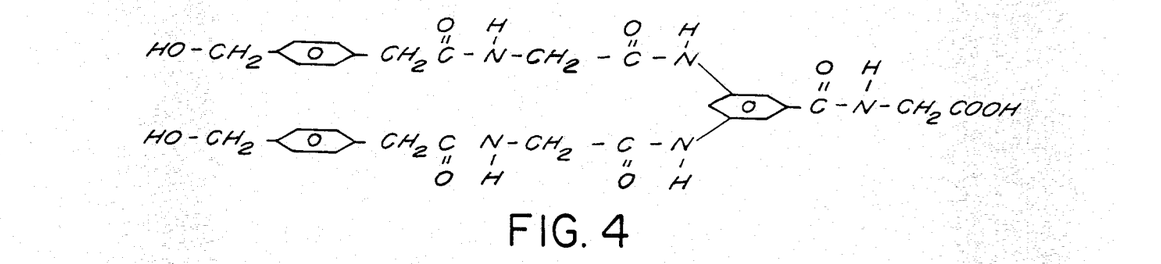
Figure 5:
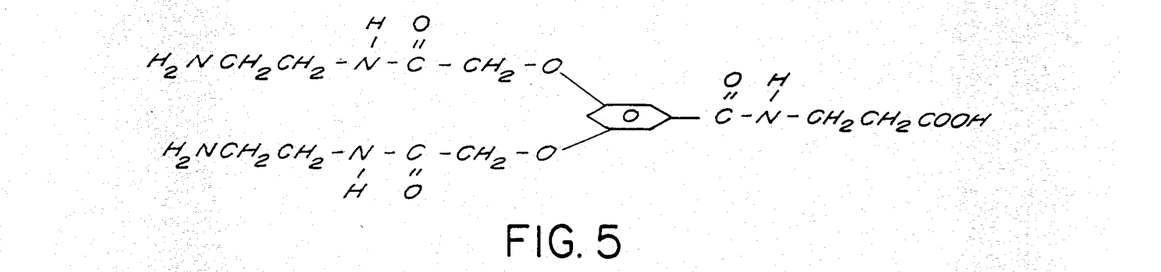

Preferred linking modules for use in the practice of this invention are those used to prepare the products shown in FIGS. 1 and 2. Their structures are shown in FIGS. 4 and 5. They are preferred since they are easily prepared from readily available reagents by known processes and may be produced in high yield.

The methods of this invention may be employed in the same manner as conventional solid phase synthesis. They can be used, for example, to prepare the various peptides and proteins which have been prepared by the earlier methods including, for example, angiotensin I and II, bradykinin, gramicidin, neurotensin, tuftsin, and vasopressin, as well as fragments of such materials as casein, elastin, fibrin and insulin. The synthesis of oxytocin is shown in the Examples. The synthesis is also useful for the preparation of proteins not present in nature such as betabellin 1, the synthesis of which is shown in Example 8. They can be prepared with or without the kinking segment. These proteins are useful for a variety of practical applications, for example they will serve as carriers for various chemical and biological materials used to detect toxic agents such as nerve gases in the atmosphere or for medicinal agents for oral or parenteral administration.

Figure 6:
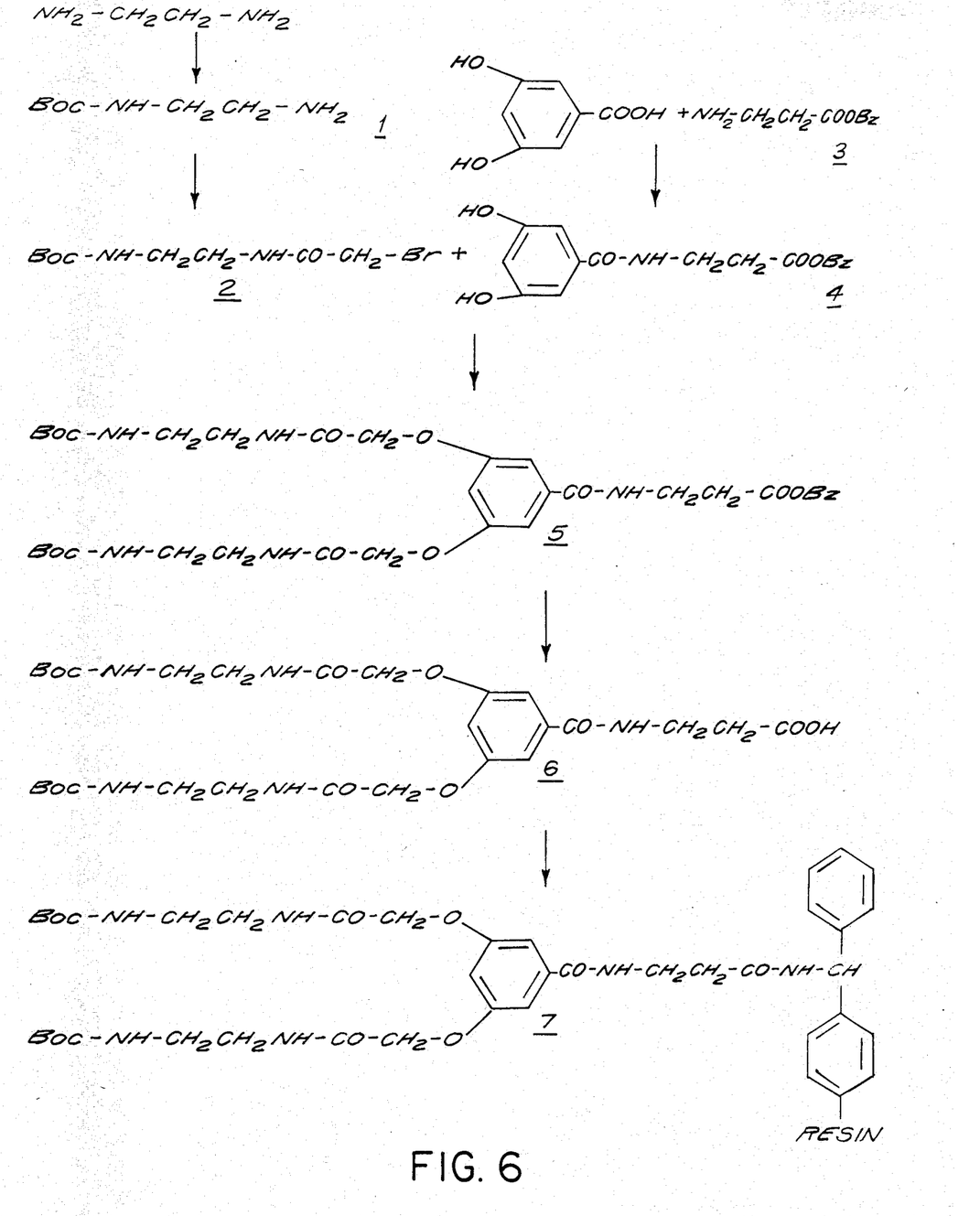
Figure 7:
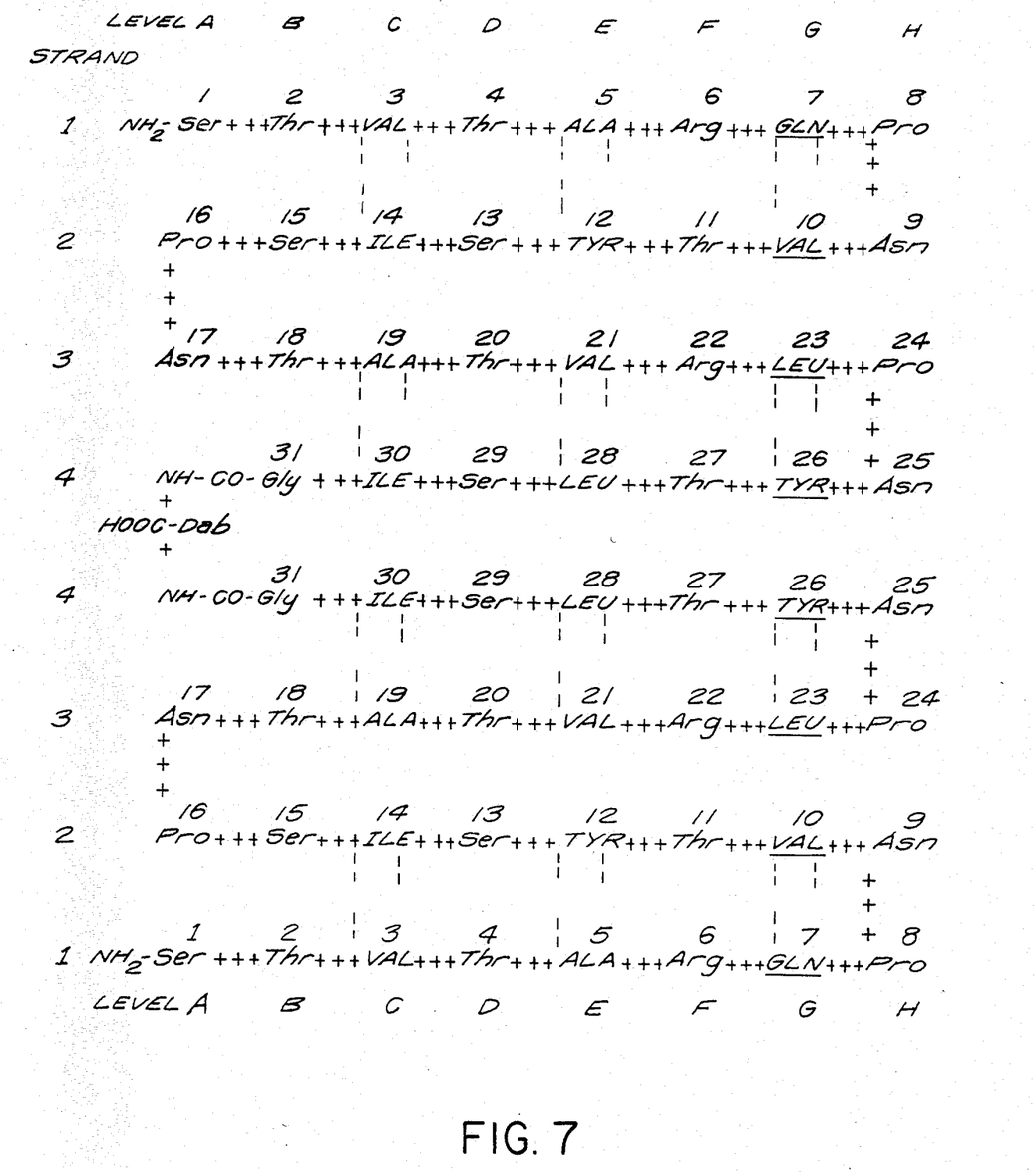

The structure of betabellin is shown in FIG. 7. It consists of two 31-residue chains of amino acids linked through Compound 6 of FIG. 6 (with the Boc groups removed) as the linking segment. In the figure covalent bonds are indicated by the positive signs and hydrogen bonds by the dotted lines.

The following non-limiting examples are given by way of illustration only. The syntheses described in Examples 1 through 6 are shown in FIG. 6.

Melting points were determined between glass cover slips with a Fisher-Johns apparatus and are uncorrected. Thin-layer chromatograph (TLC) was carried out on glass plates coated with an 0.25-mm layer of silica gel GF (Analtech, Newark, (Del.). IR spectra were measured in $CHCL_3$ solution with a Perkin-Elmer Model 237 grating spectrometer. Proton NMR spectra were taken in $CDCL_3$ or methyl sulfoxide $d_6$ solution at 60 MHz with a Nicolet 7T spectrometer. Chemical shifts are reported in parts per million downfield from internal tetramethylsilane.

EXAMPLE 1

2-(tert-Butoxycarbonylamido)ethyl Amine

A solution of ethylenediamine (50 g, 0.92 mol) in 200 ml of 4-dioxane and 100 ml of water was cooled to 0° C. and bis(tert-butoxycarbonyl)carbonate (50 g, 0.23 mol) was added. The reaction mixture was stored at room temperature for eighteen hours, and the solvent was evaporated. The oily residue was dissolved in a 200 ml ethyl acetate-100 ml water mixture. The ethyl acetate solution was washed with water until TLC showed the absence of ethylenediamine and kept at 0° C. for 18 hours. A second crop of di-Boc compound crystallized out and was filtered off. The filtrate was evaporated and the residual oil dissolved in water (100 ml) and extracted with ethyl acetate twice. The water layer was evaporated in vacuo to give Compound 1 as an oil. The original aqueous layer above was evaporated, the residue was dissolved in ethyl acetate and washed with water to remove the ethylenediamine. The combined organic phase was dried and evaporated in vacuo to provide compound 1. The combined yield of Compound 1 was 15 g (40% yield) as an oil:
(NMR (CDCl$_3$) 1.5 (s,9H), 2.8 (m,2H) 3.2 (q,2H), 5.5 ppm (m,3H).

EXAMPLE 2

Bromoacetyl 2-(tert-Butoxycarbonamido)ethylamide

A solution of Compound 1 (10.4 g, 81 mmol) and triethylamine (8.14 g, 81 mmol) in tetrahydrofuran (200 ml) was cooled to −78° C. A solution of bromoacetylbromide (16.3 g, 81 mmol) in tetrahydrofuran (10 ml) was cooled to −78° C. and added dropwise over 15 minutes. The mixture was stirred for 1 hour at −78° C. and another 2 hours at room temperature. The triethylamine hydrobromide salt was filtered off and washed with THF and the combined THF solutions were evaporated. The residue was dissolved in ethyl acetate (500 ml). The solution was washed with ice-cold 0.5N HCl and saturated aqueous sodium chloride, dried over anhydrous magnesium sulfate, and evaporated. The residue was triturated with hexane and recrystallized from ethyl acetate and hexane to provide compound 2 as a white powder: 15.6% (77% yield). mp 88°–89° C.; IR (CHCl$_3$) 3500, 1700 and 1680 cm$^{-1}$; NMR (CDCl$_3$) 1.5 (s,9H), 3.4 (t,4H), 3.9 (s,2H), 5.0 (m,1H), and 7.2 ppm (m,1H); Calcd for C$_9$H$_{17}$O$_3$; C, 38.44; H, 6.096; N, 9.96; Found: C, 38.41; H, 6.11; N, 9.83.

EXAMPLE 3

Benzyl 3-Aminopropionate

A solution of beta-alanine (17.8 g, 0.2 mol), 4-toluenesulfonic acid hydrate (46 g, 0.24 mol), and benzyl alcohol (62 ml, 0.6 mol) in benzene (40 ml) was place in a Dean Stark azeotropic distillation apparatus and allowed to reflux for 10 hours. The reaction mixture was cooled to room temperature and the solid residue was mixed with ether and filtered. The solid was washed with ether and with hot ethyl acetate to provide compound 3: 65 g (93% yield).

EXAMPLE 4

A solution of 3,5-dihydroxybenzoic acid (4 g, 26 mmol) and N-methylmorpholine (26 mmol) in dimethylformamide (100 ml) was cooled to 0° C. Isobutyl chloroformate (26 mmol) was cooled to 0° C. and added, and the resulting slurry was stirred for 30 minutes. A solution of beta alanine benzyl ester tosylate (26 mmol) and N-methylmorpholine (26 mmol) in dimethylformamide (30 ml) was cooled to 0° C. and added. The reaction mixture was stirred for 18 hours and evaporated under vacuum. The residue was dissolved in ethyl acetate and the solution was washed with 0.5N HCl, saturated aqueous sodium chloride, dried over anhydrous magnesium sulfate and evaporated to provide compound 4 as an oil: 6.0 g (73% yield) IR (CHCl$_3$) 3300, 1710 and 1600 cm$^{-1}$; NMR (CDCl$_3$) 2.8 (t,2H), 3.7 (q,2H), 5.2 (s,2H), 6.6 (t.,1H) 6.9 (d,2H), 7.4 (s,5H), and 7.9 ppm (t,1H); Calcd for C$_{17}$H$_{17}$O$_5$N: C, 64.75; H, 5.43; N, 4.44; Found: C, 64.65; H, 5.60; N, 4.24.

EXAMPLE 5

A solution of 5-3[dihydroxybenzamido]propionate (1.0 g, 3.17 mmol), potassium fluoride (3.68 g, 63.4 mmol) and N-bromoacetyl-N'-boc-ethylenediamine (1.78 g, 6.34 mmol) in 25 ml of dimethyl formamide was stirred at 50° C. for 1 day. Additional bromo compound (0.356 g, 1.26 mmol) was added and the mixture stirred another day. The progress of the reaction was followed by TLC (CHCl$_3$:CH$_3$OH:HOAc 9:1:0.1 by volume). The slurry was cooled to room temperature and evaporated under reduced pressure. The residue was dissolved in ethyl acetate (50 ml) and water (50 ml). The organic phase was washed twice with 50 ml portions of aqueous sodium chloride, dried over anhydrous magnesium sulfate and evaporated. The crude crystals (2.61 g) were recrystallized from ethyl acetate to provide pure compound 5 as a white powder: 1.68 g (74% yield); mp 151°–152° C.; TLC Rf 0.64 (CHCl$_3$CH$_3$OH/HOAc 85:10:5); IR (CHCl$_3$) 3450, 2900, 1700 and 1685 cm$^{-1}$); MS (m/e) 715.3431; Calcd for C$_{35}$H$_{49}$O$_{11}$N$_5$: C, 58.73; H, 6.89; N, 9.78; Found: C, 58.70; H, 6.88; N, 9.64.

EXAMPLE 6

Compound 5 (2 g, 2.8 mmol) was dissolved in methanol (10 ml) and acetic acid (10 ml). To this was added 10% palladium on charcoal (0.5 g) suspended in water (2 ml). Ammonium formate (1 g) was dissolved in a minimum amount of water and added to the slurry. The reaction mixture was stirred for 18 hours at room temperature. The catalyst was filtered off and washed thoroughly with methanol. The filtrate was evaporated to dryness and the residue dissolved in ethyl acetate. The solution was washed with saturated aqueous sodium chloride solution, dried over anhydrous magnesium sulfate, and evaporated. The residue was recrystallized from ethyl acetate and hexane to provide compound 6 as a white powder: 1.179 (66.8% yield); mp 158°–159° C.; TLC Rf 0.35 (CHCl$_3$/CH$_3$OH//HOAc); Calced for C$_{28}$H$_{43}$O$_{11}$N$_5$: C, 53.75; H, 6.92; N, 11.19; Found C, 53.55; H, 7.06; N, 11.10.

EXAMPLE 7

Synthesis Betabellin 1

A solution of Compound 6 (2 mmol) and N,N'-dicyclohexylcarbodiimide (2 mmol) in dichloromethane (15 ml) was added to beads of 1-amino-1-phenylmethylcopoly(styrene-1% divinylbenzene) (1.0 g, 0.5 mmol of amino groups). The mixture was agitated for 2 days, filtered, and washed with dichloromethane. Then the 31 amino acid residues in each of the two chains of betabellin (see FIG. 7 were assembled on the linking segment starting with the carboxyl terminus by the repetitive methodology of solid phase peptide synthesis. The addition of each residue required the performance of a series of five synthetic steps, which taken together comprised one synthetic cycle. Each synthetic cycle consisted of the following five steps: deprotection, neutralization, coupling, neutralization, coupling. Thus, the second and fourth steps were the same, as were the third and fifth steps. During deprotection, the beads were agitated with a solution of trifluoroacetic acid (10 ml) and dichloromethane (10 ml), filtered, and washed with dichloromethane. During neutralization, the beads were agitated with a solution of triethylamine (1 ml) and dichloromethane (9 ml), filtered, and washed with dichloromethane. During coupling, the beads were agitated with a solution of the appropriate Boc-amino acid (6 mmol) in dichloromethane (10 ml) for 10 minutes, without filtering the beads a solution of N,N'-dicyclohexylcarbodiimide (6 mmol) in dichloromethane (5 ml) was added, and the beads were agitated for 4-18 hours, filtered, and washed with dichloromethane. During each synthetic cycle, the beads were coupled with the N-(tert-butoxycarbonyl) derivative of the next amino acid, starting at the carboxyl terminus of betabellin 1. After assembly of the 31-residue peptide chains on each arm of the linking module was completed, the beads were dried under vacuum to remove all organic solvent and stirred with a solution of anisole (1 ml) and liquid hydrogen fluoride (9 ml) for 30 minutes at 0° C. The HF and anisole were evaporated using a water aspirator followed by a vacuum pump. The residual beads were washed with diethyl ether and were extracted with trifluoroacetic acid. The extract was concentrated under vacuum, diluted with water, and lyophilized. The residual material, which is crude betabellin 1, is purified by chromatographic and electrophoretic procedures.

EXAMPLE 8

Synthesis of Oxytocin 3,5-Bis[N-(tert-butoxycarbonyl)glycinamido]benzoic Acid(Bis[Boc-Gly]Dab-OH)

3,5-Bis(glycinamido)benzoic acid (10 mmol), prepared by the method of Akamatsu and Furiya [J. Biochem. (Japan) 41, 317 (1954)], is added to a mixture of bis(tert-butoxycarbonyl)carbonate (20 mmol) and triethylamine (30 mmol) in tert-butanol (25 ml) and water (25 ml). The mixture is stirred for 1 day, acidified with dilute hydrochloric acid to pH 2, and diluted with ethyl acetate (50 ml). The organic phase is washed with water and evaporated to dryness to give the title acid.

Benzyl 3-[3,5-Bis[N-(tert-butoxycarbonyl)glycinamidol]benzamido]-propionate-(Bis[Boc-Gly]Dab-betaAla-OBzl)

A solution of 3,5-Bis[N-tert-butoxycarbonyl)-glycinamidol]benzoic acid (10 mmol) and N,N'-dicyclohexylcarbodiimide (10 mmol) in dichloromethane (100 ml) is kept at room temperature for 2 hours. A solution of benzyl 3-aminopropionate hydrochloride (10 mmol) and triethylamine (10 ml) in dichloromethane (50 ml) is added. The mixture is stirred for 24 hours and diluted with dilute hydrochloric acid to pH 2. The organic phase is washed with water, saturated aqueous sodium bicarbonate, and water, dried over anhydrous magnesium sulfate, and evaporated to dryness under vacuum to furnish the title ester.

3-[3,5-Bis[$N^2$-(tert-butoxycarbonyl)glycinamidol]benzamido]propionic Acid(Bis[Boc-Gly]Dab-betaAla-OH)

A solution of benzyl 3-[3,5-bis[$N^2$-(tertbutoxycarbonyl)glycinamido]benzamido]propionate (10 mmol), 88% formic acid (100 mmol), methanol (30 ml), and acetic acid (30 ml) is stirred with 10% palladium on carbon for 1 hour. The solid catalyst is filtered off and the filtrate is evaporated under reduced pressure to yield the title acid.

3-[3,5-Bis[$N^2$-(tert-butoxycarbonyl)glycinamido]benzamido]propionamidomethyl-polystyrene(Bis[Boc-Gly]Dab-betaAla-Resin)

Aminomethyl-copoly(styrene-1% divinylbenzene) ("resin") beads (10 g, 1.0 mmol. of amino groups per gram of resin, 200-400 mesh), prepared by the procedure of Mitchell, Kent, Erickson & Merrifield [Tetrahedron Lett., 3795(1976)], is swelled in dimethylformamide (80 ml). A solution of 3-[3,5-bis[N-tertbutoxycarbonyl)glycinamido]propionic acid (10 ml) and N,N'-dicyclohexylcarbodiimide (10 mmol) in dimethylformamide (50 ml) is kept at room temperature for 1 hour and added to the swelled resin. The mixture is gently tumble agitated for 2 days and filtered. The beads are washed with dimethylformamide and dichloromethane. Residual aminomethyl groups are acetylated by shaking the resin with a mixture of acetic anhydride (50 ml) and pyridine (50 ml) for 1 day. The beads are washed with dimethylformamide and dichloromethane to give the title resin.

3-[3,5-Bis(glycinamido)benzamido]propionamidomethyl-polystyrene(Bis[Gly]Dab-betaAla-Resin)

3-[3,5-Bis]N-tert-butoxycarbonyl)glycinamidobenzamido]proprionamidomethyl-polystyrene beads (10 g) are swelled in a mixture of trifluoroacetic acid (50 ml) and dichloromethane (50 ml). The mixture is gently tumble agitated for 1 hour and filtered. The beads are washed with dichloromethane, a solution of triethylamine (10 ml) in dichloromethane (90 ml), and dichloromethane to provide the title resin.

3-[3,5-Bis[$N^2$-[4-glycloxymethyl]phenylacetyl]-glycinamido]benzamido]-propionamidomethyl-polystyrene(Bis[Boc-Gly-Opa-Gly]Dab-betaAla-Resin)

3-[3,5-Bis(glyclamino)benzolyamino]propionamidomethyl]-polystyrene beads (10 g, 20 mmol) are swelled in dichloromethane (70 ml) is added. A solution of 4-[N-(tert-butoxycarbonyl)glycyloxmethyl]-phenyl acetic acid, prepared by the procedure of Tam, Kent, Wong & Merrifield [Synthesis 955 (1979)], (40 mmol) in dichloromethane (100 ml). The mixture is gently tumble agitated for 10 min, a solution of N,N'-dicyclohexylcarbodiimide (40 mmol) in dichloromethane (40 mmol) in dichloromethane (40 ml) is added, and agitation is continued for 2 days. The beads are washed with dimethylformamide and dichloromethane and swelled in a mixture of trifluoroactic acid (50 ml) and dichloromethane (50 ml). The mixture is gently tumble agitated for 1 hour and filtered. The beads are washed with dichloromethane, a solution of triethylamine (10 ml) in dichloromethane (90 ml), and dichloromethane to provide the title resin.

3-[3,5-Bis[N²[4-[S-(4-methylbenzyl)-L-cysteinyl-O-(2-bromobenzyloxycarbonyl)L-tyrosyl-L-isoleucyl-L-glutaminyl-L-asparaginyl-S-(4-methylbenzyl)-L-cysteinyl-LL-cysteinyl-L-proly-L-leucylglycyloxymethyl]-phenylacetyl]glycinamido]benzamido-]propionamidomethyl-polystyrene(Bis[Cys(4-MeBzl)-Tyr(2-BrZ)Ile-Gln-Asn-Cys(4-MeBzl)-Pro-Leu-Gly-Opa-Gly]Dab-betaAla-Resin)

The remaining eight amino acids of oxytocin are assembled on the linking segment starting with the carboxyl terminus by the repetetive methodology of solid phase peptide synthesis. The addition of each residue requires the performance of a series of five synthetic steps, which taken together comprise one synthetic cycle. Each synthetic cycle consists of the following five steps: neutralization, coupling, neutralization, coupling, deprotection. Thus, the first and third steps are the same, as are the second and fourth steps. During neutralization, the beads (10 g, 20 mmol of amino groups) are agitated with a solution of triethylamine (10 ml) and dichloromethane (90 ml), filtered, and washed with dichloromethane. During coupling, the beads are agitated with a solution of the appropriate Boc-amino acid (60 mmol) in dichloromethane (100 ml) for 10 minutes; without filtering the beads, a solution of N,N'-dicyclohexylcarbodiimide (60 mmol) in dichloromethane (50 ml) is added; and the beads are agitated for 4 hours, filtered, and washed with dichlorom methane. During deprotection, the beads are agitated with asolution of trifluoroaceticacid (50 ml) and dichloromethane (50 ml), filtered, and washed with dichloromethane. During the first synthetic cycle, 3-[3,5-bis[N²[4-glycyloxymethyl]phenylacetyl]glycinamidolbenzamido]propionamidomethyl-polystyrene is coupled with N-(tert-butoxycarbonyl)-L-leucine. During the following synthetic cycles the resulting beads are coupled in turn with N-(tert-butoxycarbonyl)-L-proline, N-(tert-butoxycarbonyl)-S-(4-methylbenzyl)-L-cysteine, N-(tert-butoxycarbonyl)-L-asparagine, N-(tert-butoxycarbonyl)L-glutamine, N-(tert-butoxycarbonyl)-L-isoleucine, N-(tert-butoxycarbonyl)-O-(2-bromobenzyloxycarbonyl)-L-tyrosine, and N-(tert-butoxycarbonyl)-S-(4-methylbenzyl)-L-cysteine to furnish the title resin.

Oxytocin(Cys-Tyr-Ile-Gln-Asn-Cys-Pro-Leu-Gly-NH², cyclic disulfide form)

Beads (10 g) of bis[Cys(4-MeBzl)-Tyr(2-BrZ)-Ile-Gln-Asn-Cys(4-MeBzl)-Pro-Leu-Gly-Opa-Gly]Dab-betaAla-resin are mixed with a solution of methanol (50 ml) saturated with gaseous anhydrous ammonia at 40° C. The mixture is sealed in a pressure bottle, stirred for 2 days at room temperature, and evaporated to remove all of the ammonia and methanol. The residue is extracted with dimethyl formamide and the extracts are evaporated underreduced pressure. The residue is stirred with a solution of anisole (1 ml) and liquid hydrogen floride (9 ml) for 30 minutes at 0° C. The HF and anisole are evaporated using a water aspirator followed by a vacuum pump. The residual material, which is crude oxytocin in the reduced form, is oxidized to the cyclic disulfide form and purified by chromatographic procedures.

What is claimed is:

1. In the solid phase method for the synthesis of peptides or proteins in which an amino acid or protein is joined to a solid support and the desired peptide or protein is formed by stepwise addition of amino acid or peptide residues to produce the desired peptide or protein, the improvement comprising initially binding a trifunctional module to the solid support through one of its functional groups and thereafter synthesizing two identical peptides or proteins by stepwise addition of amino acid or peptide residues to each of the remaining pair of functional groups.

2. The method of claim 1 in which the original trifunctional module is joined through each of said remaining pair of functional groups to two additional trifunctional modules through one functional group on each molecule and thereafter synthesizing four identical peptides or proteins by stepwise addition of amino acid or peptide residues to each of the remaining two pairs of functional groups.

3. The method of claim 2 including the steps of joining additional pairs of trifunctional modules until the number of functional groups available as substrates for the stepwise addition of amino acids and protein is 8, 16, 32 or 64.

4. The method of claims 1, 2 or 3 in which the module includes a spacer segment.

* * * * *

UNITED STATES PATENT AND TRADEMARK OFFICE
CERTIFICATE OF CORRECTION

PATENT NO. : 4,515,920
DATED : May 7, 1985
INVENTOR(S) : Bruce W. Erickson

It is certified that error appears in the above—identified patent and that said Letters Patent is hereby corrected as shown below:

Column 1 between "SYNTHESIS OF PEPTIDES AND PROTEINS" and "BACKGROUND OF THE INVENTION" insert ---This invention was made with Government support under Contract N00014-83-K-0600 awarded by the Department of the Navy. The government has certain rights in the invention.---

Signed and Sealed this

Thirty-first Day of October, 1989

*Attest:*

DONALD J. QUIGG

*Attesting Officer*       *Commissioner of Patents and Trademarks*